US010508007B2

(12) United States Patent
Czwaluk et al.

(10) Patent No.: US 10,508,007 B2
(45) Date of Patent: Dec. 17, 2019

(54) HEIGHT-ADJUSTMENT DEVICE AND METHOD FOR OPERATING AN AGITATING DEVICE

(71) Applicant: UTS Biogastechnik GmbH, Hallbergmoos (DE)

(72) Inventors: Andreas Czwaluk, Vechta (DE); Johann Bierer, Dorfen (DE)

(73) Assignee: UTS BIOGASTECHNIK GMBH, Hallbergmoos (DE)

( * ) Notice: Subject to any disclaimer, the term of this patent is extended or adjusted under 35 U.S.C. 154(b) by 63 days.

(21) Appl. No.: 15/524,291

(22) PCT Filed: Nov. 5, 2015

(86) PCT No.: PCT/EP2015/075837
§ 371 (c)(1),
(2) Date: May 6, 2017

(87) PCT Pub. No.: WO2016/071460
PCT Pub. Date: May 12, 2016

(65) Prior Publication Data
US 2017/0334690 A1 Nov. 23, 2017

(30) Foreign Application Priority Data
Nov. 7, 2014 (DE) .................. 10 2014 116 246

(51) Int. Cl.
*B66D 5/14* (2006.01)
*C12M 1/107* (2006.01)
(Continued)

(52) U.S. Cl.
CPC .............. *B66D 5/14* (2013.01); *B66D 5/32* (2013.01); *C12M 21/04* (2013.01); *C12M 27/06* (2013.01); *Y02E 50/343* (2013.01)

(58) Field of Classification Search
CPC ............ B66D 5/14; B66D 5/32; C12M 21/04; C12M 27/06; Y02E 50/343
See application file for complete search history.

(56) References Cited

U.S. PATENT DOCUMENTS

| 2,684,833 | A | 7/1954 | Benson | |
|---|---|---|---|---|
| 7,862,008 | B2* | 1/2011 | Woodruff | B60P 7/083 |
| | | | | 254/218 |
| 2006/0186388 | A1* | 8/2006 | Thune et al. | B66D 1/54 |
| | | | | 254/347 |

FOREIGN PATENT DOCUMENTS

| AT | 358223 B | 8/1980 |
|---|---|---|
| AU | 7928591 A | 9/1991 |

(Continued)

*Primary Examiner* — Gautam Prakash (57) ABSTRACT

Height adjusting device (1) for adjusting the height of an agitating device (2) in a digester (101) of a biogas plant (100), biogas plant (100) comprising a digester (101), a support unit (10), a displacement member (6), an agitating device (2), and a height adjusting device, and method for operating an agitating device (2). The height adjusting device comprises a housing unit (4), a drum device (5) rotatably accommodated on the housing unit (4), and a displacement member (6). The displacement member (6) is in functional connection with the drum device (5) and the agitating device (2) and the displacement member (6), depending on the direction of rotation of the drum device (5), can be wound onto the drum device (5) or unwound from the drum device (5) in sections, so that the agitating device (2) can be displaced upwardly or downwardly. Furthermore a fixing device (7) is provided which is suitable and configured to fix the drum device (5) at least temporarily to prevent the displacement member (6) from unwinding if the displacement member (6) is not retained tautly between the drum device (5) and the agitating device (2).

18 Claims, 3 Drawing Sheets

(51) Int. Cl.
*C12M 1/06* (2006.01)
*B66D 5/32* (2006.01)

(56) References Cited

FOREIGN PATENT DOCUMENTS

| | | |
|---|---:|---|
| DE | 3345643 A1 | 6/1985 |
| DE | 3500783 A1 | 7/1986 |
| DE | 19732198 C1 | 10/1998 |
| DE | 202006010384 U1 | 11/2006 |
| DE | 202007002835 U1 | 7/2007 |
| DE | 202009005024 U1 | 9/2009 |
| DE | 102011120851 A1 | 6/2013 |
| EP | 0894525 A2 | 2/1999 |
| EP | 2689830 A1 | 1/2014 |
| WO | 2008104320 A2 | 9/2008 |
| WO | 2014015948 A2 | 1/2014 |

\* cited by examiner

HEIGHT-ADJUSTMENT DEVICE AND METHOD FOR OPERATING AN AGITATING DEVICE

CROSS-REFERENCE TO RELATED APPLICATIONS

This application is a National Stage Entry of International Application No. PCT/EP2015/075837, filed Nov. 5, 2015, which claims the benefit of German Application Serial No. 102014116246.3, filed Nov. 7, 2014.

The present invention relates to a height adjusting device which is in particular suitable for adjusting the height of at least one agitating device in a digester of a biogas plant. The height adjusting device comprises at least one housing unit, at least one drum device rotatably accommodated at the housing unit, and at least one displacement member. The drum device is preferably provided by a cable spool and the displacement member is in particular configured as a cable. The displacement member is in functional connection with the drum device and the agitating device and, depending on the direction of rotation of the drum device, it can at least partially be wound onto the drum device or unwound from the drum device. This allows to displace the agitating device upwardly or downwardly. The invention moreover relates to a biogas plant having at least one agitating device having at least one such height adjusting device and to a method for operating an agitating device having such a height adjusting device.

A digester of a biogas plant is as a rule provided with at least one agitator with which to thoroughly mix the substrate received in the digester. This allows to improve the efficiency of the biogas plant since a homogeneous, thoroughly mixed substrate can be provided, so-called floating sludge layers can be better avoided, and gas can be expelled.

To achieve a particularly homogeneous, thorough mixing of the substrate the agitator tends to be disposed on a mast where the agitator is retained traversable in height.

A height-traversable agitator moreover is very easy to maintain since the agitator can simply be traversed upwardly to a servicing position for maintenance and/or repairs.

For adjusting the height the agitator tends to be retained traversable on the mast and it may be displaced upwardly and downwardly by means of a cable. For lowering the agitator the cable is unwound from a cable spool and for lifting the agitator it is wound onto the cable spool.

However, this height adjustment shows the disadvantage that given specific circumstances the agitator may get stuck or jammed on the mast. Then the agitator cannot be lowered any further.

If a user still continues to unwind the cable from the cable spool, the cable length increases between the cable spool and the jammed agitator. In the worst-case scenario the cable may then become entangled in the agitator.

This involves the risk of the cable getting damaged or even destroyed. Moreover, other lines guided to the agitator with the cable may likewise be damaged or destroyed. In the aforedescribed cases it is very complicated and expensive to restart the agitator or the digester.

It is therefore the object of the present invention to provide a height adjusting device and a biogas plant having such a height adjusting device ensuring safe operation.

This object is solved by a height adjusting device having the features of claim 1, by a biogas plant having the features of claim 20, and by a method for operating an agitating device having the features of claim 21. Preferred specific embodiments and configurations of the invention are the subjects of the subclaims. Further advantages and features of the invention can be taken from the exemplary embodiments.

The height adjusting device according to the invention is in particular suitable for adjusting the height of at least one agitating device in a digester of a biogas plant. The height adjusting device comprises at least one housing unit, at least one drum device rotatably accommodated at the housing unit, and at least one displacement member. The displacement member is in functional connection with the drum device and the agitating device wherein, depending on the direction of rotation of the drum device, the displacement member can at least partially be wound onto the drum device or unwound from the drum device. This allows to displace the agitating device upwardly or downwardly. Furthermore at least one fixing device is provided which is suitable and configured to fix the drum device at least temporarily to at least prevent the displacement member from unwinding if the displacement member is not retained tautly between the drum device and the agitating device.

A drum device according to the invention is in particular understood to mean a cable spool which is preferably accommodated rotatably around an axle. The axle is preferably aligned substantially horizontally and accommodated on the housing unit of the height adjusting device.

The fact that the displacement member is in functional connection with the drum device and the agitating device means in particular according to the invention that the displacement member is preferably directly or else indirectly connected with the two aforementioned members. If the displacement member is not directly connected with the drum device and the agitating device, connectors may in particular be provided to be conveniently employed for fastening the displacement member to the drum device and/or to the agitating device.

According to the invention the fixing device achieves that the displacement member is prevented from unwinding from the drum device such that the agitating device cannot be displaced any farther downwardly. According to the invention it is in particular provided that unwinding is automatically prohibited as soon or as long as the displacement member is not or no longer retained taut between the drum device and the agitating device.

Taut is in particular understood to mean that the displacement member is slightly tensioned at least in sections. Further according to the invention, taut is understood to mean that the displacement member unwinding from the drum device is not, or not substantially, longer than is the distance between the agitating device and the drum device.

Upwardly and downwardly displaceable is in particular understood to mean according to the invention that the agitating device is upwardly and downwardly displaceable relative to the drum device, i.e. it can be moved toward or away from it.

The height adjusting device according to the invention offers many advantages. It is a considerable advantage that the inventive height adjusting device allows to achieve that the displacement member can only then unwind further from the drum device if the agitating device is simultaneously displaced further downwardly. This effectively prevents damage to the agitating device which might otherwise occur due to maloperation and/or malfunction.

If the displacement member unwinds further although the agitating device is not simultaneously displaced downwardly, then the displacement member is not held taut between the drum device and the agitating device. In the worst-case scenario the displacement member might then get into the rotor of the agitating device and become entangled in the agitator blades. This may damage the rotor or else may damage or even sever the displacement member and/or any supply lines guided to the agitating device together with the displacement member. The maintenance work and expenditure arising therefrom would increase enormously.

Continued unwinding of the displacement member although the agitating device is not simultaneously displaced downwardly may be caused by maloperation or malfunction. Maloperation of the height adjusting device might mean that a user for example unwinds the displacement member further from the drum device, neglecting to first stop the rotor of the agitating device. The rotational movement of the rotor urges the agitating device against the mast accommodating the agitating device. The static friction so generated is sufficient for prohibiting further lowering of the agitating device. Then the displacement member would continue unwinding and in the worst-case scenario it would finally become entangled in the rotor.

In the case of malfunction of the system the agitating device may for example get jammed so as to prohibit further lowering of the agitating device. Again, the displacement member and/or the supply lines may be damaged or severed.

The height adjusting device according to the invention effectively prevents this by way of only allowing the displacement member to further unwind from the drum device as long or as soon as the displacement member is held tautly between the drum device and the agitating device.

Preferably the displacement member comprises at least one cable and/or a chain. The cable respectively the chain may preferably be made of metal and/or plastic at least in sections. The cable used may conveniently be a tape, a cord, a genuine rope, or a belt, showing a flat, round, or angular configuration.

Particularly preferably the agitating device is accommodated on a support unit along which the agitating device can be displaced upwardly and downwardly. Preferably the height adjusting device is likewise accommodated on, or at least assigned to, the support unit. The support unit is conveniently substantially positioned from the bottom to the top with the support unit preferably positioned substantially in the vertical. Particularly preferably the height adjusting device and the agitator can be rotated or pivoted together about the vertical axis.

In preferred embodiments the fixing device comprises at least one disk device and at least one fixing member. A functional connection between the fixing member and the disk device can then be established at least temporarily. In this way it can be achieved that in specific circumstances the fixing device prohibits further unwinding of the displacement member from the spool device. However, the drum device may be released as soon as the displacement member is once again retained tautly between the drum device and the agitating device.

The drum device can preferably be fixed by way of form grip and/or static friction between the disk device and the fixing member. It is preferred for adhesive forces, clamping forces, and/or locking forces to act between the disk device and the fixing member.

The disk device is preferably assigned to the drum device. The disk device may particularly preferably be provided on the same shaft as is the drum device wherein the disk device can then advantageously block rotation of the shaft.

Preferably the disk device forms at least part of, or is integrally manufactured with, the drum device. Thus it can be readily ensured that when the disk device is fixed, the drum device is likewise prohibited from moving further at least in one direction.

Preferably the disk device has the form of a brake disk and the fixing member comprises at least one brake pad. In this advantageous configuration the fixing device operates in analogy to a disk brake. At least one brake disk face is provided with at least one brake pad which may be urged against the brake disk as soon as the displacement member ceases to be retained tautly between the drum device and the agitating device.

Particularly preferably the disk device is configured as a toothed disk. Preferably this toothed disk shows at least one and in particular a plurality of teeth. If more than one tooth is provided, the teeth are preferably evenly distributed over the circumference of the toothed disk.

Preferably at least one of the teeth of the toothed disk is oriented radially outwardly. Preferably all of the teeth are oriented outwardly and substantially evenly distributed over the circumference.

In advantageous specific embodiments the fixing member is pivotally accommodated on the housing unit relative to the drum device and/or the disk device. In this way it is achieved that the fixing member can establish a functional connection with the disk device if the displacement member is no longer retained tautly between the drum device and the agitating device. To this end the fixing member pivots in the direction of the disk device so as to block the same. As soon as the displacement member is taut again, the fixing member can pivot away from the disk device, thus releasing the drum device.

Preferably the fixing device comprises at least one biasing device. Such a biasing device may in particular comprise at least one spring and in particular at least one tension spring. Then the biasing device is preferably assigned to the fixing member.

In advantageous configurations the biasing device is then disposed between the fixing member and the housing unit. Then the biasing device is in particular disposed so that the biasing device pulls the fixing member in the direction of the disk device. Thus, the fixing member may in particular fix the drum device automatically in a functional connection with the disk device if no counterpressure is applied against the tensile force of the biasing device.

Preferably the fixing member comprises at least one appendix, hook, and/or pawl. This configuration may in particular be employed advantageously if the drum device is achieved by form grip between the disk device and the fixing member.

Preferably the fixing member comprises at least one cable guide. This allows for one, to ensure a secure guide for the displacement member. For another, it may also be ensured that the fixing member makes contact with the disk device if the displacement member is not retained tautly. Moreover it may be achieved that the fixing member pivots away if the displacement member is retained tautly. This is achieved by way of the displacement member showing different contact points at the cable guide, depending on whether it is taut or slack.

Particularly preferably the fixing device comprises at least one freewheel. This allows to ensure that the drum device cannot unwind any further as long as the displacement member is not retained tautly between the drum device and the agitating device. Moreover it can be achieved that the drum device can still wind up again although the displacement member is not retained tautly.

Preferably the freewheel is provided by at least one momentum grade on at least one tooth of the toothed disk. Thus, form grip between a tooth of the disk device and the fixing member can achieve a blocking action. The momentum grades, however, allow continued rotation of the disk in the other direction to allow the drum device to wind up further even if the displacement member is not retained tautly.

Preferably at least one transmission device is assigned to the drum device. The transmission device is preferably disposed on the housing unit or accommodated in the housing unit at least in sections. This transmission device allows to drive the drum device for example by means of a motor.

The biogas plant according to the invention comprises at least one digester and at least one agitating device which is displaceably disposed on at least one support unit by means of at least one displacement member. Furthermore at least one height adjusting device as described above is provided.

The biogas plant according to the invention also offers many advantages. A considerable advantage is that the biogas plant operates particularly reliably. In particular the agitating devices disposed in the digester can be safely height-adjusted without resulting in damage due to displacement members retained less than tautly.

The method according to the invention is suitable for operating an agitating device in a digester of a biogas plant wherein the agitating device can be displaced along a support unit by means of a height adjusting device. The height adjusting device is in particular configured as it has been described above. According to the invention the drum device of the height adjusting device is fixed at least temporarily in at least one direction of rotation by means of the fixing device so as to in particular automatically prevent the displacement member of the height adjusting device from unwinding further if the displacement member is not retained tautly between the agitating device and the drum device.

The method according to the invention also offers the advantages described above. A secure and reliable operation of an agitating device in the digester of a biogas plant is in particular provided. The agitating device can be safely displaced upwardly and downwardly without risking damage due to a non-taut displacement member in the case of malfunction or maloperation.

Further advantages and features of the present invention can be taken from the exemplary embodiments which will be discussed below with reference to the enclosed figures.

Figure 1:
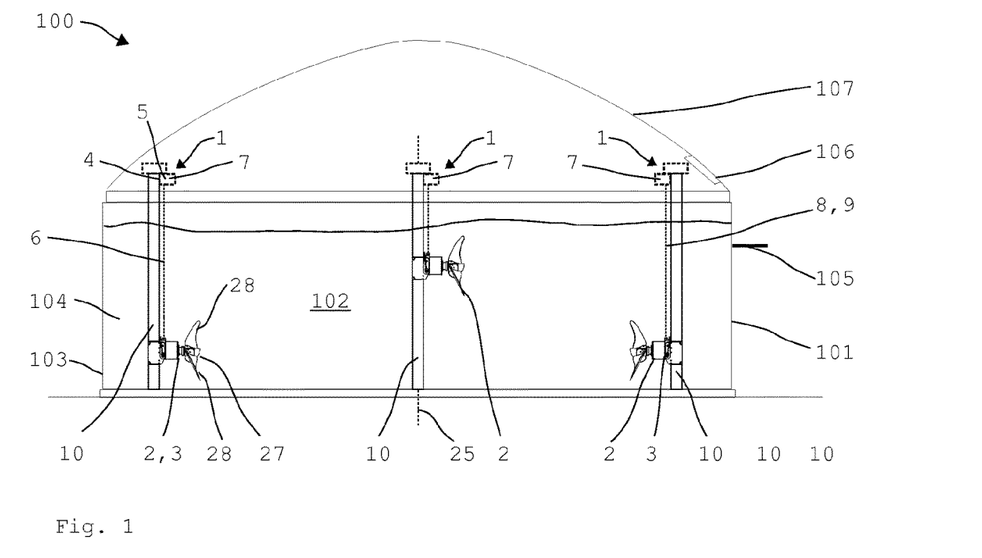
FIG. 1 a purely schematic illustration of a biogas plant comprising an inventive height adjusting device.

FIG. 1 is a purely schematic illustration of a digester 101 of a biogas plant 100 in a sectional view. In this embodiment the digester 101 comprises a digester wall 103 bordering the digester interior 102. The digester interior 102 is suitable to receive substrate 104 for fermenting.

The right side of the digester 101 purely schematically illustrates a platform 105 providing access to a servicing opening 106 in the digester roof 107. The agitating device 2 can be readily accessed through this servicing opening 106 in particular for maintenance purposes. The agitating device 2 shown is configured as an agitator 3.

The presently illustrated digester 101 is provided with a total of three agitators 3 which achieve a particularly homogeneous, thorough mixing of the substrate 104. The illustrated exemplary embodiment includes a servicing opening 106 for each of the agitators 3 wherein only the servicing opening 106 for the agitator 3 on the right is illustrated purely schematically.

Each of the three agitating devices 2 can be displaced upwardly and downwardly along a supporting device 10. Moreover the agitators 3 can also be pivoted about the longitudinal axis 25 of the pertaining support unit 10. This allows to achieve a particularly effective and homogeneous thorough mixing of the substrate 104 in the digester interior 102.

Each of the support units 10 comprises at its top end a height adjusting device 1 comprising one drum device 5 each. The drum devices 5 are configured as cable spools 26. Each cable spool 26 receives one displacement member 6 which presently is configured as a cable 8. In other configurations the cable 8 may be provided by a chain 9 or another suitable means.

The drum device 5 allows the displacement member 6 to shift upwardly and downwardly. In this way the agitating devices 2 can be height-adjusted along the support unit 10.

Changing the height of the agitating devices 2, however, involves certain risks due to errors in application and/or malfunction. Pulling the agitating devices 2 upwardly is as a rule unproblematic. When lowering the agitating devices 2, however, although the displacement member 6 unwinds from the drum device 5, it may happen that the agitating device 2 is not displaced downwardly along the support unit 10.

This may happen in the case of malfunction for example if the agitating device 2 is jammed on the support unit 10. Maloperation of the biogas plant 100 may likewise result in that the agitating device 2 is not displaced downwardly along the support unit 10 although the displacement member 6 unwinds from the drum device 5. This may happen among other things if a user wishes to displace the agitating device 2 downwardly while the rotor 27 of the agitating device 2 is still rotating.

The rotation of the rotor 27 generates a certain static friction between the agitating device 2 and the support unit 10 which may in certain circumstances prohibit displacement of the agitating device 2 along the supporting device 10. In the worst-case scenario the displacement member 6 may then unwind from the drum device 5 although the agitating device 2 is not displaced further downwardly. This would cause the displacement member 6 to not be retained tautly between the drum device 5 and the agitating device 2.

When the agitating device 2 is not displaced along with the unwinding displacement member 6, the length of the displacement member 6 between the drum device 5 and the agitating device 2 keeps increasing so that in the worst-case scenario the displacement member 6 may get into the rotor 27 of the agitating device 2. Then the agitator blades 28 of the rotor 27 may make contact with the displacement member 6 and wind it up due to the rotation of the rotor 27.

This might cause damage to the displacement member 6 or to supply lines running in parallel. In the very worst-case scenario the displacement member 6 and/or the supply lines may tear apart.

The supply lines are not shown in detail in the embodiment illustrated. A supply line may for example be a current-carrying line for operating the agitating device 2 or else a hydraulic line for operating the agitating device 2.

If the displacement member 6 is damaged or torn apart then it may be very difficult to convey the agitating device 2 along the support unit 10 in the direction of the servicing opening 106 for repairs. In the worst-case scenario, operation of the biogas plant 100 must be stopped and the digester 101 emptied out so as to install a new displacement member 6 on the agitating device 2 through access to the digester interior 102.

The height adjusting device 1 according to the invention can effectively and reliably prevent this kind of damage since the height adjusting device 1 according to the present invention comprises a fixing device 7 prohibiting unwinding of the displacement member 6 if the displacement member 6 is not retained tautly between the drum device 5 and the agitating device 2.

The height adjusting device 1 according to the invention is purely schematically shown in detail in the FIGS. 2 to 12.

Figure 2:
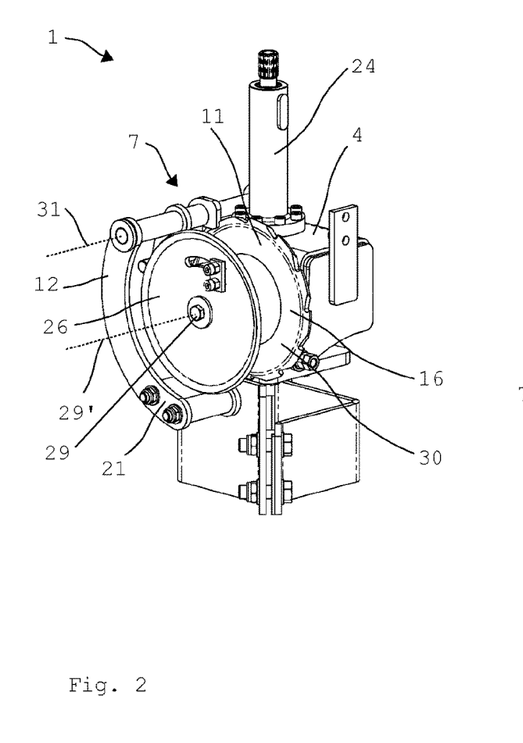
FIG. 2 a perspective view of an inventive height adjusting device in a purely schematic illustration.

FIG. 2 illustrates the height adjusting device 1 according to the invention purely schematically in a perspective view. The height adjusting device 1 comprises a housing unit 4 which rotatably accommodates a drum device 5. The drum device 5 is pushed onto an axle 29 that is oriented substantially horizontally.

The drum device 5 has assigned to it a gear transmission 24 for rotating the drum device 5 from outside of the digester 101. The gear transmission 24 is received in or on the housing unit 4.

The drum device 5 serves to accommodate a displacement member 6 which is at best indicated purely schematically in the following Figures. The displacement member 6 is provided to be a cable 8 in the presently illustrated embodiment. Or else it may for example be configured as a chain 9. The cable 8 may be manufactured from any suitable material which should in particular be suitable to be employed in the substrate 104.

The height adjusting device 1 comprises a fixing device 7 to prohibit further unwinding of the displacement member 6 if it is not tensioned or not retained tautly between the drum device 5 and the agitating device 2.

Depending on the embodiment the fixing device 7 serves to prohibit either by static friction and/or by form grip further unwinding movement of the drum device 5.

In the embodiment shown the fixing device 7 comprises a disk device 11 and a fixing member 12. In the embodiment shown the disk device 11 is configured as a toothed disk 16 which can block the drum device 5 by way of form grip with the fixing member 12.

The toothed disk 16 provides a bearer 30 of the drum device 5. Other configurations may also provide an additional component as a disk device 11 which is then accommodated for example on the same axle 29 as is the drum device 5. A disk device 11 may also effectively prohibit rotation of the drum device 5 in this way.

The fixing member 12 of the fixing device 7 is received on the housing unit 4 to be pivotable relative to the disk device 11. The pivot axis 31 in the embodiment shown is provided about parallel to the axis 29 of the drum device 5.

The fixing member 12 also comprises a cable guide 21 which securely guides the displacement member 6 and which moreover causes the pivoting motion of the fixing member 12 for fixing or releasing the drum device 5.

Figure 3:
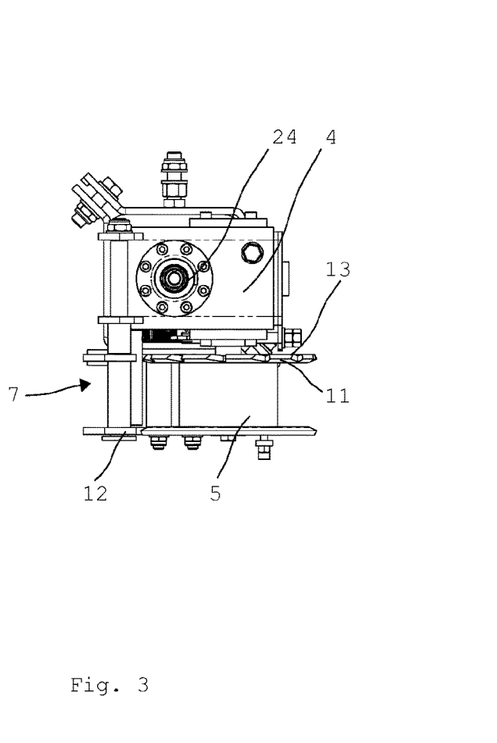
FIG. 3 a purely schematic illustration of an inventive height adjusting device in a top view.

FIG. 3 illustrates the height adjusting device 1 according to FIG. 2 in a purely schematic top view. Again one can recognize the transmission device 24 through which the drum device 5 may be rotated. The drum device 5 comprises the disk device 11 of the fixing device 7 wherein the disk device 11 configured as a toothed disk 16 is provided on the side 13 of the drum device 5 facing the housing unit 4. The fixing member 12 is accommodated on the housing unit 4 to pivot about the pivot axis 31.

Figure 4:
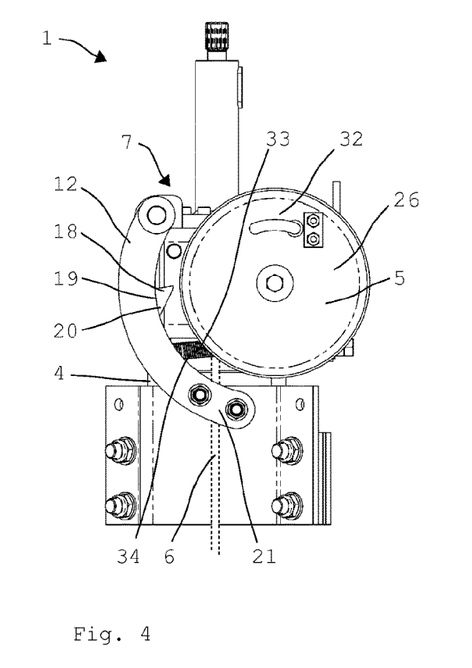
FIG. 4 a purely schematic illustration of an inventive height adjusting device in a front view.

In FIG. 4 the height adjusting device 1 according to the invention is shown in a purely schematic front view. One looks at the outer bearer 32 of the drum device 5 and the fixing member 12 pivotally accommodated on the housing unit 4.

In the presently shown embodiment the disk device 11 is configured as a toothed disk 16 with the disk device 11 not visible in this view. The fixing member 12 comprises an appendix 18 which is configured as a hook 19 respectively pawl 20.

In the presently shown illustration the fixing member 12 is pivoted away from the disk device 11 so that the appendix 18 does not make contact with the disk device 11. This allows the drum device 5 to freely rotate in both directions.

The fixing member 12 swings out automatically if the displacement member 6 is retained tautly between the drum device 5 and the agitating device 2. Then the displacement member 6 runs in the cable guide 21 of the fixing member 12 so that it is displaced away from the disk device 11. Then the fixing member 12 is counter to the tractive force of the biasing member 33 of the fixing device 7.

In the presently shown embodiment the biasing member 33 is configured as a spring 34 respectively tension spring 34. The spring 34 serves to automatically establish contact of the fixing member 12 with the disk device 11 if the displacement member 6 is not retained tautly between the drum device 5 and the agitating device 2.

Then the tensile force of the spring 34 causes the fixing member 12 to be pulled in the direction of the disk device 11 as soon as the displacement member 6 ceases to apply a counterforce against the tensile force of the spring 34 by way of the cable guide 21.

Figure 5:
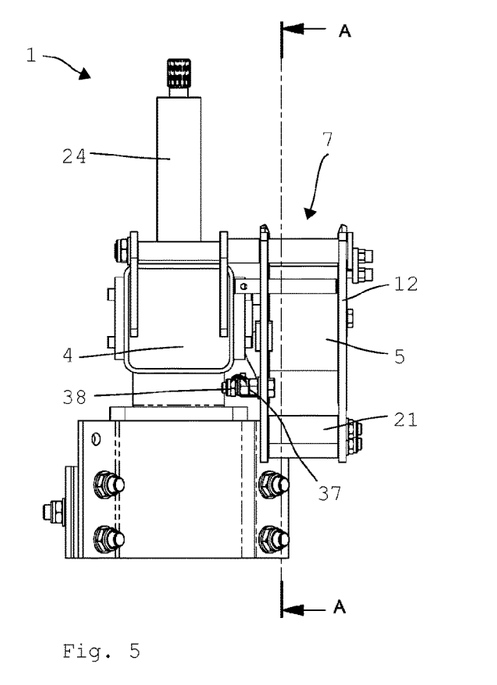
FIG. 5 a purely schematic illustration of an inventive height adjusting device in a side view.

In FIG. 5 the height adjusting device 1 according to the invention is illustrated in a purely schematic side view from the left. The sectional plane A-A inserted in FIG. 5 is shown in FIG. 6 purely schematically in a front sectional view.

Figure 6:
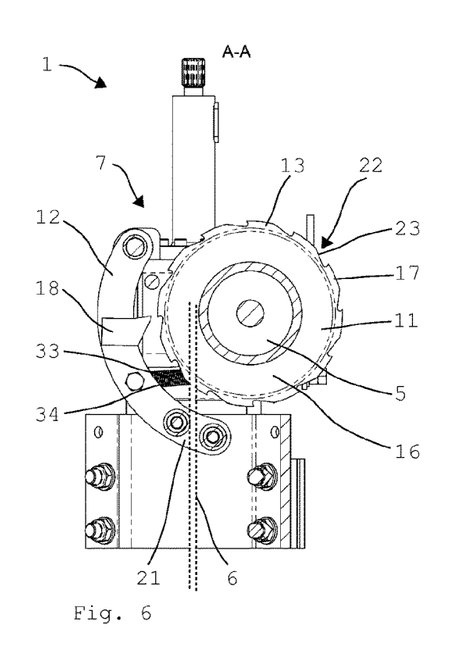
FIG. 6 a purely schematic illustration of an inventive height adjusting device in a front view along the sectional plane A-A in FIG. 5.

One can recognize in FIG. 6 the disk device 11 of the fixing device 7 which is provided as one piece with the drum device 5. The disk device 11 is provided on the side 13 of the drum device 5 facing the housing unit 4 and is configured as a toothed disk 16.

When the displacement member 6 is retained tautly, the displacement member 6 applies a counterforce against the tensile force of the spring 34 through the cable guide 21 so as to cause the fixing member 12 to pivot away from the disk device 11. Due to this the pawl 20 of the fixing member 12 ceases to contact a tooth 17 of the toothed disk 16.

In this situation the drum device 5 can freely rotate in both directions to thus enable the agitating device 2 to be displaced upwardly and downwardly along the support unit 10.

Figure 7:
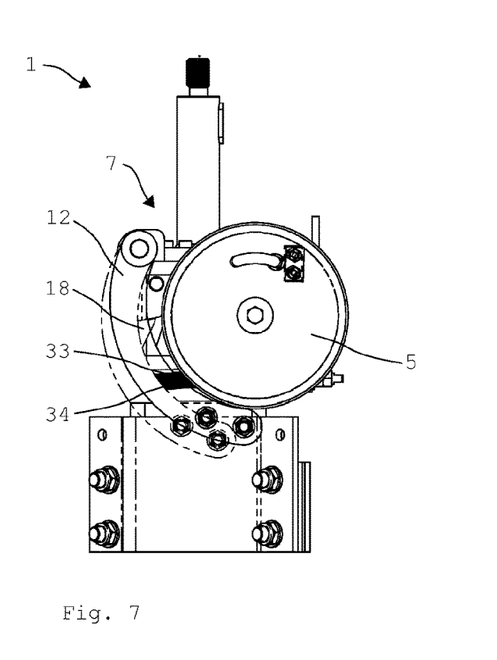
FIG. 7 another purely schematic illustration of an inventive height adjusting device in a front view.

FIG. 7 illustrates purely schematically the movement of the fixing member 12 as it occurs if the displacement member 6 ceases to be retained taut between the drum device 5 and the agitating device 2.

Then the fixing member 12 is pulled in the direction of the disk device 11 due to the tensile force of the biasing device 33.

Figure 8:
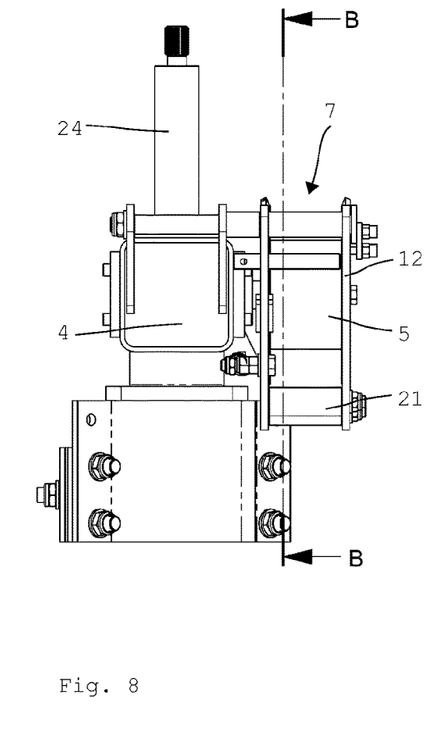
FIG. 8 another purely schematic illustration of an inventive height adjusting device in a side view.
Figure 9:
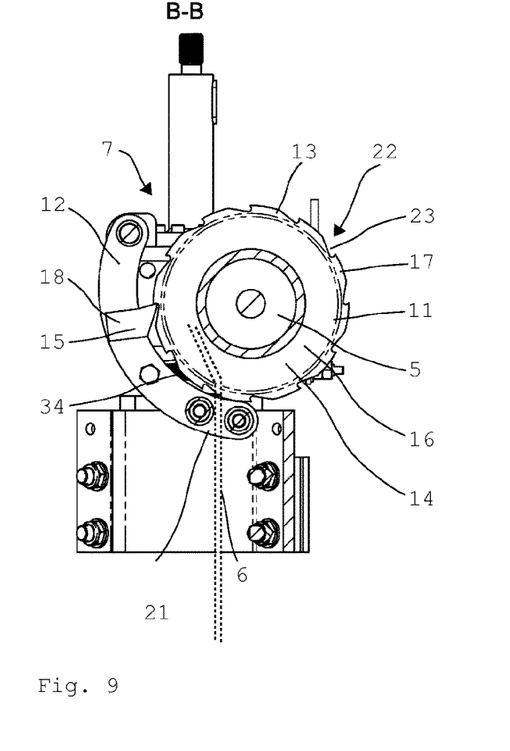
FIG. 9 another purely schematic illustration of an inventive height adjusting device in a front view along the sectional plane B-B in FIG. 8.

The blocked situation of the drum device 5 is illustrated purely schematically in the FIGS. 8 and 9.

When the displacement member 6 is not retained tautly between the agitating device 2 and the drum device 5 then the fixing member 12 of the fixing device 7 is pivoted in the direction of the disk device 11. This occurs due to the tensile force of the biasing member 33 of the fixing device 7.

In the presently shown embodiment the disk device 11 is configured as a toothed disk 16. In this embodiment an appendix 18 of the fixing member 12 being in functional connection with at least one tooth 17 of the toothed disk 16 may result in a form grip owing to which the drum device 5 is prevented at least from further unwinding.

In the presently shown embodiment a freewheel 22 is provided on the fixing device 7. This freewheel 22 is provided by way of momentum grades 23 on the teeth 17 of the toothed disk 16. The momentum grade 23 achieves that, although rotation of the drum device 5 is blocked in the one direction by the pawl 20 being in functional connection with a tooth 17 of the toothed disk 16, the displacement member 6 can still wind up onto the drum device 5.

In another embodiment not shown in detail the disk device 11 may be provided by a brake disk 14 wherein the fixing member 12 then has at least one brake pad 15 which when in functional connection with the brake disk 14 prevents rotation of the drum device 5 in at least one direction at least temporarily. This embodiment is purely schematically indicated in FIG. 9.

Figure 10:
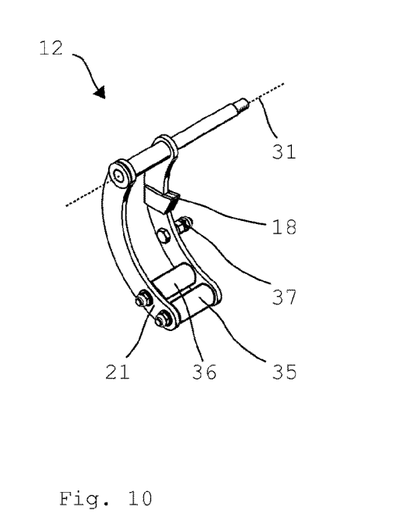
FIG. 10 a purely schematic illustration of a fixing member in a perspective view.

FIG. 10 purely schematically illustrates an embodiment of a fixing member 12 in a perspective view.

The fixing member 12 is retained pivotally around the pivot axis 31 and comprises an appendix 18 which is configured as a hook 19 respectively pawl 20. The pawl 20 is disposed on the fixing member 12 so that as the fixing member 12 swivels the pawl 20 may establish a functional connection with the disk device 11.

In the presently shown embodiment the fixing member 12 moreover comprises a cable guide 21 which is presently provided by a pair of rollers 35, 36.

Moreover one recognizes a fastener 37 to which one side of the biasing member 33 can be fastened. The other side of the biasing member 33 may be conveniently fastened to the housing unit 4 so that the fixing member 12 is pulled in the direction of the disk device 11 by way of the tensile force of the biasing member 33 if the displacement member 6 is not retained tautly between the agitating device 2 and the drum device 5.

Figure 11:
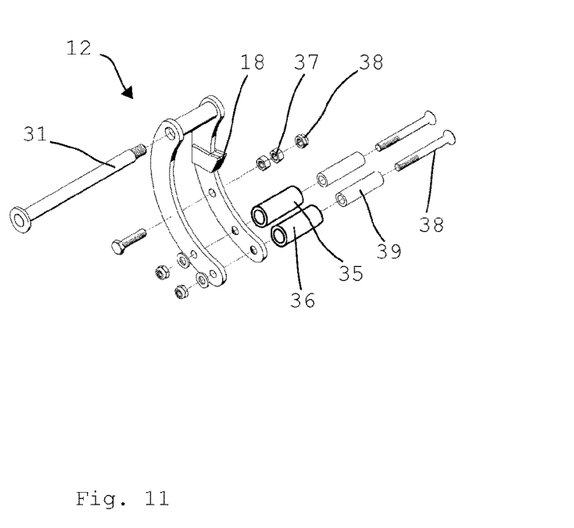
FIG. 11 a purely schematic illustration of the fixing member according to FIG. 10 in an exploded view.

The fixing member 12 according to FIG. 10 is illustrated in FIG. 11 purely schematically in an exploded view. One can recognize the detailed structure of the described embodiment of the fixing member 12.

The fastener 37 is provided by a screwed connection 38. The rollers 35, 36 of the cable guide 21 in the embodiment shown are manufactured of plastic, these rollers 35, 36 being provided on metal rollers 39 which are accommodated on the fixing member 12 by means of screwed connections 38.

1 height adjusting device
2 agitating device
3 agitator
4 housing unit
5 drum device
6 displacement member
7 fixing device
8 cable
9 chain
10 support unit
11 disk device
12 fixing member
13 side 36 roller
14 brake disk
15 brake pad
16 toothed disk
17 tooth
18 appendix
19 hook
20 pawl
21 cable guide
22 freewheel
23 momentum grade
24 transmission device
25 longitudinal axis
26 cable spool
27 rotor
28 agitator blade
29 axle
29' axis
30 bearer
31 pivot axis
32 bearer
33 biasing member
34 spring, tension spring
35 roller
37 fastener
38 screwed connection
39 roller
100 biogas plant
101 digester
102 digester interior
103 digester wall
104 substrate
105 platform
106 servicing opening
107 digester roof

The invention claimed is:

1. A height adjusting device for adjusting the height of at least one agitating device in a digester of a biogas plant comprising at least one support unit, wherein the agitating device is accommodated on the support unit along which it can be displaced upwardly and downwardly, at least one housing unit, at least one drum device rotatably accommodated at the housing unit and at least one displacement member, wherein the displacement member is coupled at a first end to the drum device and is coupled at an opposing end to the agitating device and wherein rotation of the drum device causes the displacement member to be at least partially be wound onto the drum device or unwound from the drum device, causing the agitating device to be displaced upwardly or downwardly depending on the direction of rotation of the drum device, and at least one fixing device, wherein the fixing device comprises at least one disk device and at least one brake, wherein the at least one brake engages with the disk device to fix the drum device at least temporarily to inhibit the displacement member at least from unwinding if the displacement member is not retained tautly between the drum device and the agitating device, wherein the at least one brake is retained on the housing unit and is pivotable relative to the drum device and/or the disk device.

2. The height adjusting device according to claim 1, wherein the displacement member comprises at least a cable and/or chain.

3. The height adjusting device according to claim 1, wherein the at least one brake engages the at least one disk device by way of form grip and/or static friction.

4. The height adjusting device according to claim 1, wherein the at least one disk device is assigned to the drum device.

5. The height adjusting device according to claim 1, wherein the at least one disk device is at least part of the drum device.

6. The height adjusting device according to claim 1, wherein the at least one disk device is provided on the side of the drum device facing the housing unit.

7. The height adjusting device according to claim 1, wherein the at least one disk device is configured as a brake disk and that the at least one brake comprises at least one brake pad.

8. The height adjusting device according to claim 1, wherein the at least one disk device is configured as a toothed disk.

9. The height adjusting device according to claim 8, wherein at least one tooth of the toothed disk is facing radially outwardly.

10. The height adjusting device according to claim 1, wherein the at least one brake is biased toward the at least one disk device.

11. The height adjusting device according to claim 10, wherein the at least one brake is biased toward the at least one disk device by a spring disposed between the at least one brake and the housing unit.

12. The height adjusting device according to claim 1, wherein the at least one brake comprises at least one appendix, hook and/or pawl.

13. The height adjusting device according to claim 1, wherein the at least one brake comprises at least one cable guide.

14. The height adjusting device according to claim 1, wherein the fixing device comprises at least one freewheel.

15. The height adjusting device according to claim 14, wherein the freewheel is provided by at least one momentum grade on at least one tooth of the toothed disk.

16. The height adjusting device according to claim 15, wherein the drum device has at least one transmission device assigned to it.

17. A biogas plant comprising at least one digester having a height adjusting device according to claim 1 and an agitating device, wherein the height adjusting device comprises at least one support unit, and wherein the agitating device can be displaced upwardly and downwardly on the support unit by means of the displacement member.

18. A method for operating an agitating device in a digester of a biogas plant comprising the steps of:
providing a height adjusting device according to claim 1; and
displacing the agitating device along the support unit,
wherein the drum device is fixed at least temporarily in at least one direction of rotation by means of the fixing device so that the displacement member is automatically prevented from unwinding further if the displacement member is not retained tautly between the agitating device and the drum device.

* * * * *